US008670992B2

(12) United States Patent
Morlet et al.

(10) Patent No.: US 8,670,992 B2
(45) Date of Patent: Mar. 11, 2014

(54) CLINICAL PROTOCOL DOCUMENT PRODUCTION

(75) Inventors: Laurent Morlet, Hazlemere (GB);
David Peter Wilson, Oxfordshire (GB);
Ronny Marcel Gustaaf Timmermans,
Duffel (BE); Tom Aelbrecht, Vorselaar (BE)

(73) Assignee: Janssen Pharmaceutica N.V., Beerse (BE)

(*) Notice: Subject to any disclaimer, the term of this patent is extended or adjusted under 35 U.S.C. 154(b) by 1880 days.

(21) Appl. No.: 11/166,989

(22) Filed: Jun. 24, 2005

(65) Prior Publication Data
US 2006/0293919 A1 Dec. 28, 2006

(51) Int. Cl.
*G06Q 10/00* (2012.01)
*G06Q 50/00* (2012.01)

(52) U.S. Cl.
USPC .................................... 705/2; 705/3

(58) Field of Classification Search
USPC ........................................ 705/2–3
See application file for complete search history.

(56) References Cited

U.S. PATENT DOCUMENTS

| 5,077,666 | A | * | 12/1991 | Brimm et al. | 705/2 |
| 5,619,708 | A | * | 4/1997 | Ho | 715/224 |
| 5,734,883 | A | | 3/1998 | Umen et al. | 395/601 |
| 5,963,967 | A | | 10/1999 | Umen et al. | 707/513 |
| 5,991,782 | A | | 11/1999 | Miyagawa et al. | 707/513 |
| 6,014,135 | A | | 1/2000 | Fernandes | 345/331 |
| 6,192,381 | B1 | | 2/2001 | Stiegemeier et al. | 707/505 |
| 6,205,455 | B1 | | 3/2001 | Umen et al. | 707/513 |
| 6,377,956 | B1 | | 4/2002 | Hsu et al. | 707/104.1 |
| 6,473,892 | B1 | | 10/2002 | Porter | 717/106 |
| 6,505,218 | B2 | * | 1/2003 | Umen et al. | 715/236 |
| 6,507,856 | B1 | | 1/2003 | Chen et al. | 707/513 |
| 2003/0109936 | A1 | | 6/2003 | Umen et al. | 700/1 |
| 2004/0006553 | A1 | | 1/2004 | de Vries et al. | 707/1 |

FOREIGN PATENT DOCUMENTS

EP 0 483 595 A2 5/1992
EP 0 832 462 B1 8/2002

OTHER PUBLICATIONS

"WordPerfect Office 2000" http://web.archive.org/web/20000229140052/http://www.corel.com/Office2000/standard.htm (1 of 3)Jun. 29, 2009 5:35:17 PM.*
Fazi, P. et al., "WITH: a System to Write Clinical Trials Using XML and RDBMS," *Proceedings of AMIA Annual Symposium—The Annual Symposium of the American Medical Informatics Association*, Nov. 9-13, 2002, 240-244, XP008075309.
Lander, S. "Structured Document Generation—A Cornerstone of Document Management," *Drug Information Journal*, 1998, 32(3), 757-760, XP002421739.
Cline, C. et al., "SGML-Based Editorial Systems," *The Seybold Report on Publishing Systems*, Jun. 28, 1993, 22(9), 19-22, XP002298721.

(Continued)

*Primary Examiner* — Minnah Seoh
(74) *Attorney, Agent, or Firm* — Woodcock Washburn LLP

(57) ABSTRACT

A clinical protocol document is produced by generating a clinical protocol document having a chart section and a text section. The chart section displays drug dosage information and medical assessment activity information in a time-activity chart format. The text section describes the drug dosage information and medical assessment activity information in a text format. Medical drug dosage information and medical assessment activity information are received via a chart user interface and the received information is automatically converted to text format for the text section of the document.

46 Claims, 9 Drawing Sheets

(56) References Cited

OTHER PUBLICATIONS

Leland, M.D.P. et al., "Collaborative Document Production Using Quilt", *ACM*, 1988, Bell Communications Research, Inc., 206-215.

Leslie, D.M., "Using Javadoc and XML to Produce API Reference Documentation", *SIGDOC*, Oct. 20-23, 2002, 104-109.

Shanmugasundaram, J. et al., "Efficiently Publishing Relational Data as XML Documents", *The VLDB Journal*, 2001, 10, 133-154.

* cited by examiner

- Issue/Report Date:
- Department:
- Document No.:

Parameters:

Genetic Testing  425
- Other
- Raritan
- None

Subjects gender  410
- Male Only
- Female Only
- Either

Dose multiplicity  415
- single dose
- single ascending
- multiple dose

Blinding model  420
- Single Blind
- Double Blind
- open-label

Case Report Form  430
- Paper
- EDC

"Trial to be conducted in"  435
- US
- EU

440

Population  445
- Healthy volunteers
- Others
- Healthy volunteers and others number of treatment groups  450 number of participants
15

TIME AND EVENTS SCHEDULE

| | Scrn. | Day -1 | \-0.5 | 0 | 20m | 40m | 1 | 1.5 | 2 | 2.5 | 3 | 4 | 6 | 8 | 12 | 24 | 36 | 48 | 72 | 96 | Follow-up |
|---|---|---|---|---|---|---|---|---|---|---|---|---|---|---|---|---|---|---|---|---|---|
| Time (hours) | | | | | | | | | | | | | | | | | | | | | |
| Informed Consent | ◆ | | | | | | | | | | | | | | | | | | | | |
| Resident in clinic | | ◆ | | | | | | | | | | | | | | | | | ◆ | | |
| Medical history/demography | ◆ | ◆ | | | | | | | | | | | | | | | | | | | |
| Physical examination | ◆ | ◆ | | | | | | | | | | | | | | | | | | ◆ | ◆ |
| Weight/temperature | ◆ | ◆ | | | | | | | | | | | | | | | | | | ◆ | |
| Serology | ◆ | | | | | | | | | | | | | | | | | | | | |
| Drug/alcohol screen (urine) | ◆ | ◆ | | | | | | | | | | | | | | | | | | | |
| Vital signs | ◆ | ◆ | ◆ | | | ◆ | ◆ | ◆ | ◆ | ◆ | ◆ | ◆ | ◆ | ◆ | ◆ | ◆ | | ◆ | | ◆ | ◆ |
| Clinical Safety Labs | ◆ | ◆ | | | | | | | | | | | | | | ◆ | | ◆ | ◆ | ◆ | ◆ |
| Testosterone and LH profile | ◆ | ◆ | | | | | | | ◆ | | | | | ◆ | ◆ | ◆ | ◆ | ◆ | ◆ | ◆ | |
| Serum glucose/TG (fasting) | | | | | | | | ◆ | | | | | | | | | | | | | |
| 12-lead ECG | ◆ | ◆ | | | | | | | ◆ | | | | | | | | | | | | |
| Cont. lead II ECG | | | | ◆ | | | | | | | | | | | | | | | | | |
| Oral dose | | | | ◆ | | | | | | | | | | | | | | | | | |
| PK plasma | | | ◆ | ◆ | ◆ | ◆ | ◆ | ◆ | ◆ | ◆ | ◆ | ◆ | ◆ | ◆ | ◆ | ◆ | ◆ | ◆ | ◆ | ◆ | |
| PK urine | | | ◆ | | | | | | | | | | | | ◆ | ◆ | | ◆ | ◆ | ◆ | |
| Target gene expression | | | ◆ | | | | | | | | | | | | ◆ | ◆ | | ◆ | ◆ | ◆ | |
| Adverse event enquiry | | | | | | | | | | | | | | | | | | | | | ◆ |
| Adverse events | ◆ | | | | | | | | | | | | | | | | | | | | |
| Concomitant medications | ◆ | | | | | | | | | | | | | | | | | | | | |

CLINICAL PROTOCOL DOCUMENT PRODUCTION

FIELD OF THE INVENTION

The invention generally relates to the production of documents. In particular, the invention relates to the production of clinical protocol documents.

BACKGROUND OF THE INVENTION

Before new drugs are allowed to be sold on the market, drug manufacturers must perform rigorous testing to show that the drugs are safe and effective. In the United States, the Food and Drug Administration (FDA) regulates such testing. In Europe, the European Union (EU) regulates such testing.

The testing of a new drug may take years before completion, may involve many people, and may generate truckloads worth of documentation. The testing generally happens over phases, with a clinical protocol being developed for each clinical trial. One of the early phases of testing, referred to as a "Phase 1" clinical trial, determines if the new drug is safe for humans. Such a Phase 1 clinical trial usually enlists several healthy volunteers to take a drug, while its effects on each volunteer is studied (e.g., vital signs may be monitored).

Before any drug is administered, a very detailed description (i.e., a clinical protocol) is developed and documented. The clinical protocol document may be reviewed by multiple levels of managers, by hospital staff, administrator, doctors, and the like. Such a review by so many parties, often causes many revisions to the clinical protocol document. Further, the clinical protocol must be approved by various people and bodies. To complicate matters further, a change in one part of the clinical protocol document, often requires revisions to multiple parts of the clinical protocol document.

For example, the clinical protocol document generally includes a chart that provides drug administration times and dosages and the times of the various medical assessments to be performed on the participant (e.g., take vital signs five minutes after administering the drug). Also, the clinical protocol document generally includes a section that provides a text description of the same information contained in the drug administration and activity chart. Thus, any revision to the drug administration and activity chart typically requires a corresponding revision in the section providing the text description of the chart.

The development of a clinical protocol document is typically performed manually using a word processing application. A drug manufacturer may test many drugs each year, thereby requiring many clinical protocols be developed. Thus, the development of a clinical protocol document for a clinical trial is generally a very time consuming, manually intensive procedure. As such, improvements are needed to assist in the production of such documents.

SUMMARY OF THE INVENTION

The following is a summary to provide a basic understanding of some aspects of the invention. This summary is not intended as an extensive overview of the invention, nor is it intended to identify key elements of the invention or to delineate the scope of the invention. Its sole purpose is to present some aspects of the invention in a simplified form as a prelude to the more detailed description presented below.

A method for producing a clinical protocol document includes generating a clinical protocol document comprising a chart section and a text section, the chart section for displaying drug dosage information and medical assessment activity information in a time-activity chart format, the text section for describing the drug dosage information and medical assessment activity information in a text format; receiving medical drug dosage information and medical assessment activity information via a chart user interface; displaying the medical drug dosage information and medical assessment activity information in the chart section of the document; generating text describing the received medical drug dosage information and medical assessment activity information; and displaying the generated text in the text section of the document.

A system for producing a clinical protocol document includes a document creation sub-system that generates a clinical protocol document comprising a chart section and a text section, the chart section for displaying drug dosage information and medical assessment activity information in a time-activity chart format, the text section for describing the drug dosage information and medical assessment activity information in a text format; a charting sub-system that: receives medical drug dosage information and medical assessment activity information via a chart user interface; and generates text describing the received medical drug dosage information and medical assessment activity information; and a user interface sub-system that displays the medical drug dosage information and medical assessment activity information in the chart section of the document; and displays the generated text in the text section of the document.

Additional features of the invention will be made apparent from the following detailed description of illustrative embodiments that proceeds with reference to the accompanying drawings.

BRIEF DESCRIPTION OF THE DRAWINGS

The foregoing summary, as well as the following detailed description of illustrative embodiments, is better understood when read in conjunction with the appended drawings. For the purpose of illustrating the invention, there is shown in the drawings illustrative embodiments of the invention; however, the invention is not limited to the specific methods and instrumentalities disclosed. In the drawings:

FIG. 4 is a screen shot of an illustrative user interface for production of a clinical protocol document, in accordance with an aspect of the invention;

FIG. 7 is a screen shot of yet another illustrative user interface for production of a clinical protocol document, in accordance with an aspect of the invention;

FIG. 9 is an illustrative time and event schedule chart user interface for production of a clinical protocol document, in accordance with an aspect of the invention.

DETAILED DESCRIPTION OF ILLUSTRATIVE EMBODIMENTS

Clinical trials typically require that a complex clinical protocol be developed and approved. A Phase 1 clinical trial may include the initial introduction of an investigational new drug into humans. These clinical trials are closely monitored and may be conducted in patients, but are usually conducted in healthy volunteer participants. The trials are typically designed to determine the safety and tolerability of the drug in humans, the side effects associated with increasing doses, and, if possible, to gain early evidence on effectiveness. During Phase 1, sufficient information about the drug's pharmacokinetics and pharmacological effects may be obtained to permit the design of well-controlled, scientifically valid, Phase 2 studies.

Phase 1 clinical trials may also be used to evaluate drug metabolism, structure-activity relationships, and the mechanism of action in humans. The trials may be used to determine which investigational drugs are used as research tools to explore biological phenomena or disease processes. The total number of participants included in Phase 1 clinical trials varies with the drug, but is generally in the range of twenty to eighty, although any number of participants may be included.

Figure 1:
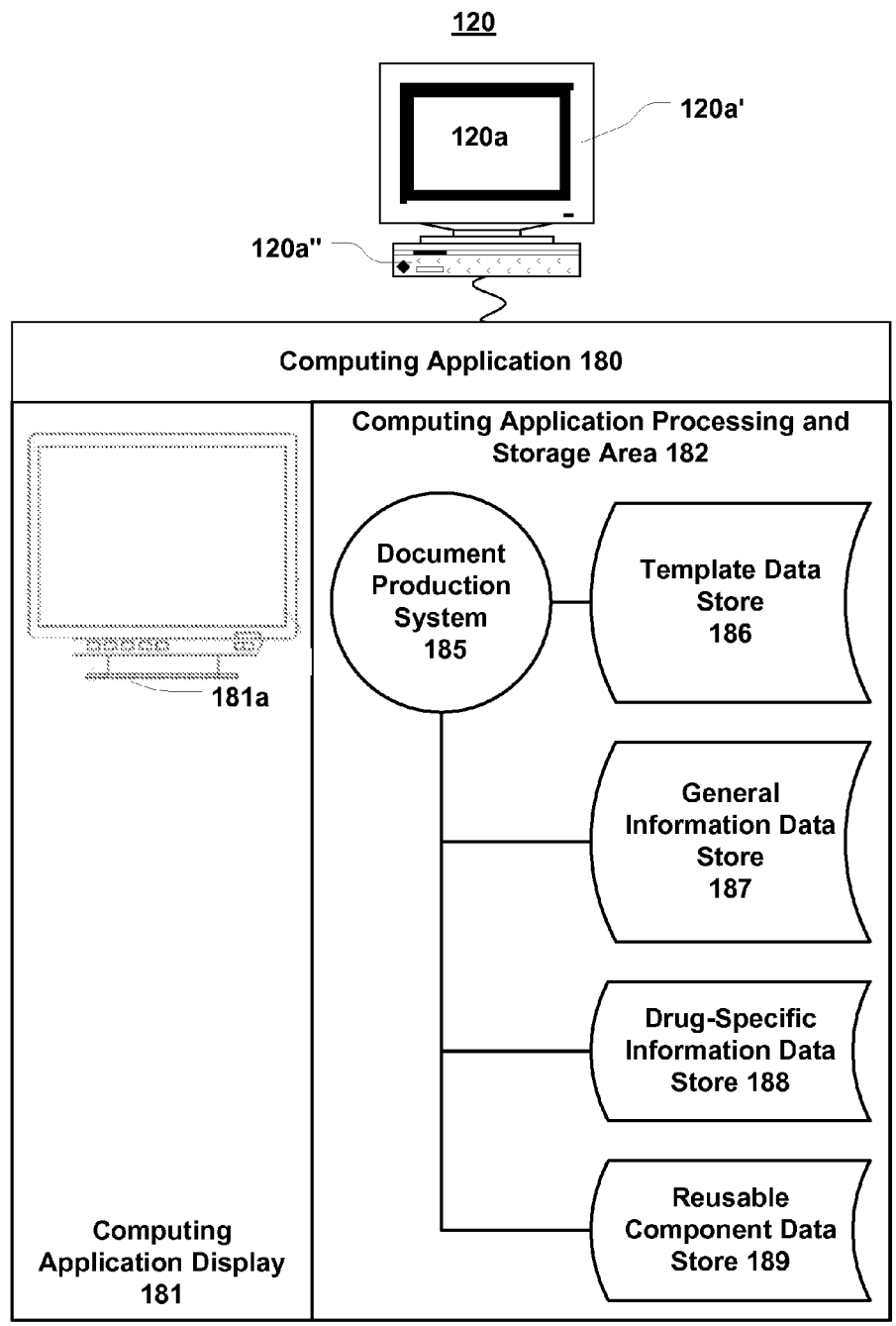
FIG. 1 is a diagram showing an illustrative computing system for generating a clinical protocol document, in accordance with an aspect of the invention.

Turning now to the production of a clinical protocol document, FIG. 1 shows an illustrative computing system 120 for producing a clinical protocol document. Computing system 120 includes computer 120a. Computer 120a includes display device 120a' and interface and processing unit 120a" having a memory (not shown). Computer 120a executes computing application 180. As shown, computing application 180 includes a computing application processing and storage area 182 and a computing application display 181. Computing application processing and storage area 182 may include clinical protocol document production system 185, clinical protocol document template data store 186, clinical protocol document general information data store 187, clinical protocol document drug specific data store 188, and clinical protocol document reusable component data store 189.

Data stores 186 through 189 may include source text that may be copied to a clinical protocol document. Alternatively, the source text may be "linked" to a clinical protocol document, such that any changes in the source text cause a corresponding change to the clinical protocol document (described in more detail below). In either event, the source text may be displayed in the clinical protocol document.

Data stores 186 through 189 may further include variables (protocol parameters) that have associated values (e.g., text string values, numeric values, and the like). The associated values may be automatically or conditionally inserted into the clinical protocol document to assist document production, as described in more detail below. Data store 186 may also include a template to organize the clinical protocol document and assist document production, as described in more detail below.

While data stores 186 through 189 are shown as being organized into a "template," "general information," "drug-specific information," and "reusable component" data store, the data stores may be organized in any convenient manner and in any convenient combinations and further into any convenient categories. The selected manner of data store organization may be implemented, for example, in accordance with revision control and security considerations. That is, template data store 186 may have the highest level of security (e.g., may only be revised upon approval of all departments involved with clinical trials), therefore, template data store 186 may be stored in a separate data store (or in a separate portion of a single data store, and the like). In such a manner, a separate data store for the template may have security authorization levels that require high levels of security authorization to make any revisions to a template. Further, drug-specific information may only require the approval of a single department, thus drug-specific information data store 188 may be stored in a separate data store (or in a separate portion of a single data store, and the like). In such a manner, the separate data store for the drug-specific information may have security authorization levels that require a different level of security authorization to make revisions to drug-specific information. Further, individual data stores may be combined into a single data store or separated into multiple data stores, if convenient.

Data stores 186 through 189, in combination with clinical protocol document production system 185 may implement systems and methods for the production of a clinical protocol document, such as, for example, a Phase 1 clinical trial protocol document. Computing application display 181 may include display content 181a which may be used for the production of a clinical protocol document. In operation, a user (not shown) may interface with computing application 180 through computer 120a. The user may navigate through computing application 180 to input, display, and generate data and information for the production of a clinical protocol document.

Figure 2:
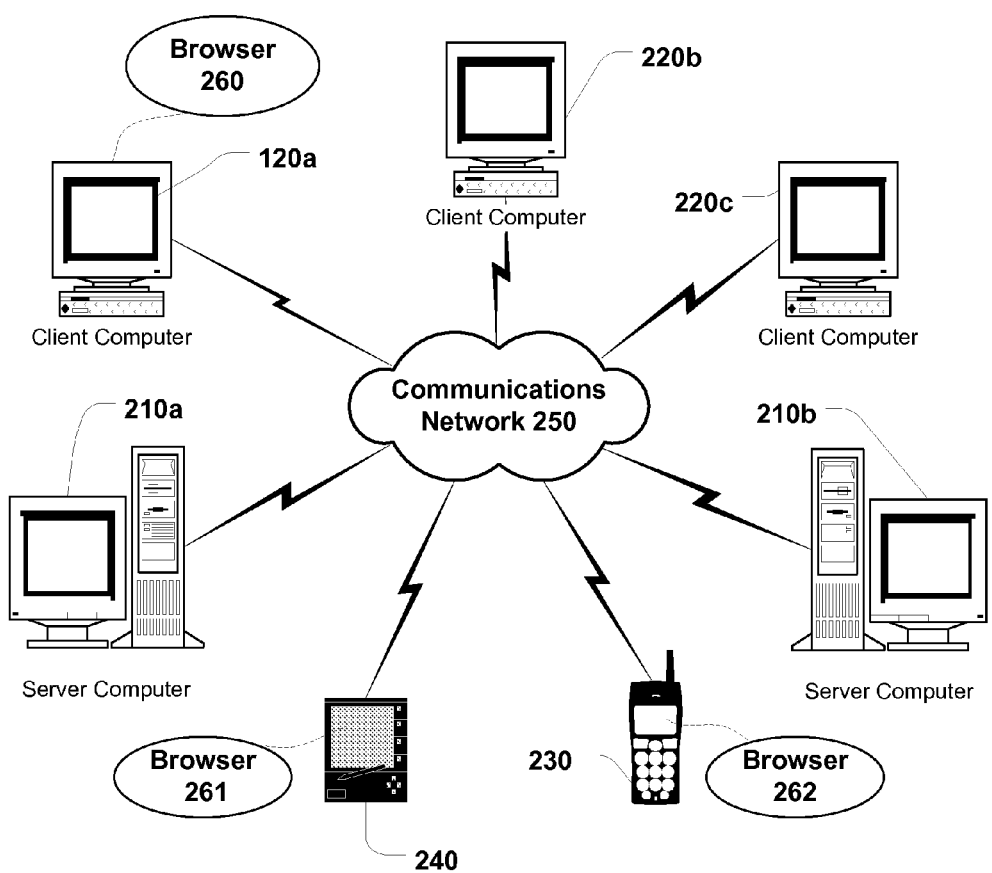
FIG. 2 is a diagram showing the illustrative computing system of FIG. 1 in communication with a network, in accordance with an aspect of the invention.

Computer 120a, described above, can be deployed as part of a computer network. In general, the description for computers may apply to both server computers and client computers (or other computers) deployed in a network environment. FIG. 2 illustrates an exemplary network environment 200 having server computers in communication with client computers, in which systems and methods for clinical protocol document production may be implemented. As shown in FIG. 2, a number of server computers 210a, 210b, etc., are interconnected via a communications network 250 with a number of client computers 120a, 220b, 220c, etc., or other computing devices, such as, a mobile phone 230, and a personal digital assistant 240. Communication network 250 may be a wireless network, a fixed-wire network, a local area network (LAN), a wide area network (WAN), an intranet, an extranet, the Internet, and the like. In a network environment in which the communications network 250 is the Internet, for example, server computers 210 can be Web servers with which client computers 120 and 220 communicate via any of a number of known communication protocols, such as, hypertext transfer protocol (HTTP), wireless application protocol (WAP), and the like. Each client computer 120 and 220 can be equipped with a browser 260 to communicate with server computers 210. Similarly, personal digital assistant 240 can be equipped with a browser 261 and mobile phone 230 can be equipped with a browser 262 to display and communicate data and information.

As computing application 180 may be implemented in a standalone computing environment (e.g., as shown in FIG. 1) or in a networked computing environment (e.g., as shown in FIG. 2), there are multiple permutations of how computing application 180 may be organized. For example, document production system 185 may reside on a single computer (e.g., computer 120a) or may be distributed over multiple computers (e.g., server computer 210a and client computer 120a). Further, document production system 185 may be accessible only via a standalone computer (e.g., as shown in FIG. 1) or may be accessible via multiple computers (e.g., server computer 210a, client computer 220b, personal digital assistant 240, and the like). Also, data stores 186 through 189 may be logically implemented in a single data store or stored in separate data stores, or any combination thereof. Moreover, data stores 186 through 189 may be physically stored in a single data store, may be redundantly stored in multiple data stores, may be distributed over multiple data stores, and the like.

Figure 3:
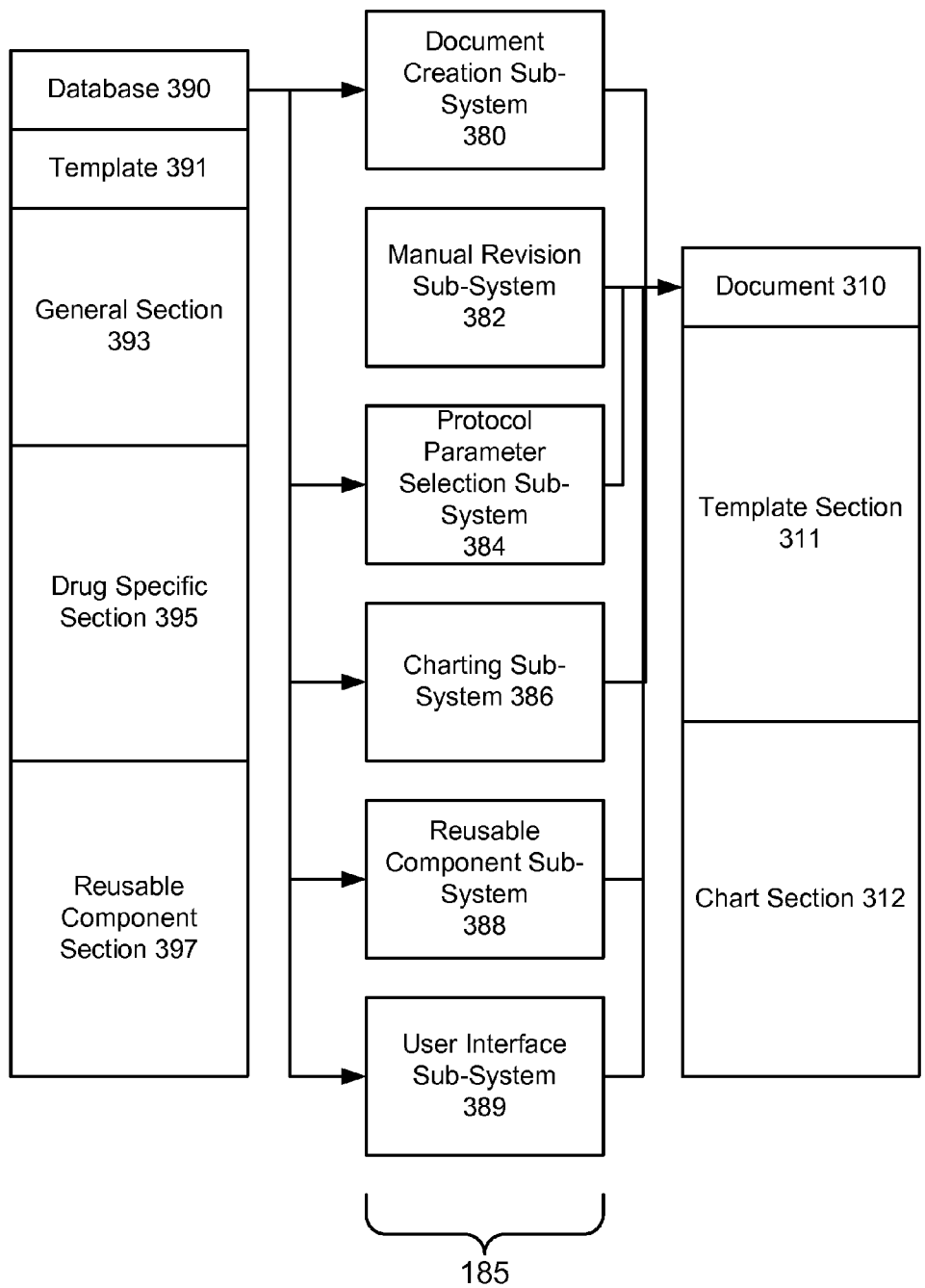
FIG. 3 is a block diagram showing an illustrative system for generating a clinical protocol document and an illustrative clinical protocol document, in accordance with an aspect of the invention.

As computing application 180 may be implemented in a standalone computing environment or in a networked computing environment, FIG. 3 shows a block diagram, without computing environment details, of one illustrative system 300 for producing a clinical protocol document 310. As shown in FIG. 3, system 300 includes a database 390, document production system 185, and document 310. Database 390 includes a template 391, a general section 393, a drug-specific section 395, and a reusable component section 397. As noted above with respect to data stores 186 through 189, database 390 may be implemented in separate sections as shown, in a single section, or in sections of any combination of categories of data.

Template 391 may be used to create document 310. Template 391 may include text and Extensible Markup Language (XML) tags to organize the template 310 and thus the clinical protocol document 310 into sections and sub-sections. XML provides a flexible way to create common information formats and share both the format and the data, for example, on the World Wide Web, intranets, and elsewhere. XML, a formal recommendation from the World Wide Web Consortium (W3C), is similar to the language of today's Web pages, the Hypertext Markup Language (HTML). Both XML and HTML contain markup symbols to describe the contents of a page or file. HTML, however, describes the content of a Web page (mainly text and graphic images) only in terms of how it is to be displayed and interacted with. For example, the letter "p" placed within markup tags indicates the start of a new paragraph. XML, on the other hand, describes the content in terms of what data is being described. For example, the word "phonenum" laced within markup tags may indicate that the following data is a phone number. This means that an XML file can be processed purely as data by a program or it can be stored with similar data on another computer or, like an HTML file, it can be displayed. For example, depending on how an application in a receiving computer handles the phone number, it could be stored, displayed, or dialed. XML is considered "extensible" because, unlike HTML, the markup symbols are unlimited and self-defining.

As shown in FIG. 3, template 391 may be used in creating a clinical protocol document 310. For such document creation, document production system 185 may include a document creation sub-system 380. Document creation sub-system 380 may interface with database 390 and may copy template 391 into a newly created document 310. With the new document 310, the user may edit document 310 without causing any changes to template 391.

Such changes may include manual user revision of document 310. As such, document production system 185 may include a document manual revision sub-system 382. Manual revision sub-system 382 allows a user to manually revise the text and XML tags of document 310. Manual revision sub-system may include an XML editor and may allow the user to selectively view or hide the XML tags of document 310. That is, document production system 185 may create a computing application display 181 that shows only the text or that shows the text and any XML tags in document 310. In this manner, the user can visually determine what the document 310 will look like without any XML tags (e.g., upon printing a final version of document 310). Also, the user can choose to see the XML tags for other purposes.

Document production system 185 may include further features that allow a user to modify document 310. For example, document production system 185 may include a protocol parameter selection sub-system 384. Protocol parameter selection sub-system 384 allows a user to select a protocol parameter and have the appropriate text automatically or semi-automatically entered into document 310. For example, protocol parameter selection sub-system 384 may interface with the user to determine that fifteen volunteers are participating in a Phase 1 clinical trial. Protocol parameter selection sub-system 384 then inserts the value 'fifteen' (or a link to the variable having the value 'fifteen') into document 310 in appropriate places, as described in more detail below. In this manner, a user can select or revise a protocol parameter and have that selection or revision propagated throughout document 310 without having to manually revise each section of document 310 that includes that particular parameter.

Document production system 185 may also include a charting sub-system 386. Charting sub-system 386 allows a user to revise dosage and medical assessment activity information in a chart form (which may thus be user-friendly) and have the dosage and medical assessment activity information from the chart automatically or semi-automatically entered into a text format in document 310, as described in more detail below. In this manner, a user can select or revise a dosage and text activity information in a user-friendly chart form without having to manually re-enter the same information in a text format (e.g., to meet an FDA or EU requirement).

Document production system 185 may also include a reusable component sub-system 388. Reusable component sub-system 388 allows a user to quickly insert text or other information into document 310, as described in more detail below. In this manner, a user can select and insert information (which may be pre-approved text) into document 310.

Document production system 185 may also include a user interface sub-system 389 that may display text (including text background) in different colors based on information associated with the text and that may prevent the user from revising some text. For example, user interface sub-system 389 may display read-only text as blue text with a dark grey background, as described in more detail below.

Returning now to template 391, to provide additional details, an illustrative template 391 is given below with XML tags shown as <XML tag> and text shown as text. Various fields within template 391 are marked with reference numerals 352 through 369. (A more detailed illustrative template is provided in Appendix A.)

---

<Company Name> <Company Name> 352
<Protocol Title> Clinical Protocol   <Protocol Title>
TABLE OF CONTENTS
 <Contact Information> CONTACT INFORMATION
  <Name> <Name> <Address> <Address>
  <Investigator Agreement> <READ ONLY> INVESTIGATOR AGREEMENT -continued I have read this agreement and agree that it contains all the necessary details for carrying out this study. I will conduct the study as outlined herein and will complete the study within the time designated. 353 <READ ONLY> 354 <Investigator Agreement> <Contact Information>
 <Overall Synopsis> <READ ONLY>
 OVERALL SYNOPSIS
  Objectives
   The <highlight> [primary] <highlight> 355 objective is
  Overview of Study Design
   <dts:function= "ProtocolInformation/Parameters/textbox[@name='number of participants']text( )"> 356 people will participate in this study.
  Pharmacogenomic Evaluations
   At the <highlight> day −1 <highlight> 357, <highlight> screening visit <highlight> 358, approximately <dts:condition="not($raritanSamples)" dts:function"=$bloodQuantity"> 359 mL of whole blood will be taken for genetic analysis from subjects who gave informed consent for this part of the study. Instructions on sample handling, labeling, and shipment are given in Attachment <highlight> Attachment Number <highlight> <READ ONLY> <Overall Synopsis>
 1. INTRODUCTION
  1.1 Background
  1.2 Overall Rationale for the Study
 <Objectives>
 2. OBJECTIVES
   <Body> Synopsis
   The <highlight> [primary] <highlight> objective is 360 <Body> <Objectives>
 <OverviewOfStudyDesign>
 3. OVERVIEW OF STUDY DESIGN
   <Body> Synopsis
    <dts:function= "ProtocolInformation/Parameters/textbox[@name='number of participants']text( )"> 361 people will participate in this study. <Body>
  3.1 Study Design
   This is a <dts:function:"ProtocolInformation/Parameters/optionbutton[@name='BlindingModel'/item/text( )"> [placebo][active]-controlled, [multicenter] study. 362
   <highlight> Place for Drag and Drop Placebo control, if none DELETE. <highlight> 363
  3.2 Study Design Rationale <OverviewOfStudyDesign>
 <StudyPopulation>
 4. STUDY POPULATION
  4.1 General Considerations
  4.2 Inclusion Criteria
   <dts:function:"ProtocolInformation/Parameters/optionbutton[@name='SubjectGender']/item/text( )"> 364
  4.3 Exclusion Criteria <StudyPopulation>
 5. RANDOMIZATION AND BLINDING
  5.1 Overview
  5.2 Procedures
 6. DOSAGE AND ADMINISTRATION
 7. COMPLIANCE
 <Concomitant Therapy>
 8. CONCOMITANT THERAPY
   [Concomitant medications are recorded at baseline and throughout the study, in the appropriate section of the <dts:function:"ProtocolInformation/Parameters/optionbutton[@name='CaseReportForm'/item/text( )"> 365] [OR] [If the administration of any concomitant therapy becomes necessary, it must be reported in the appropriate section of the <dts:function:"ProtocolInformation/Parameters/optionbutton[@name='CaseReportForm'/item/text( )"> 366]
 <Concomitant Therapy>
 9. STUDY EVALUATIONS
  9.1 Study Procedures
  9.2 Pharmacokinetic Evaluations
  9.3 Efficacy Evaluations
  9.4 Efficacy Criteria
  9.5 Safety Evaluations
   <dts:function= "$clinicalLaboratoryHematologyTables"> 367
   <dts:function= "$clinicalLaboratoryBiochemistryTables"> 368
   <dts:function= "$clinicalLaboratoryUrinalysisTables"> 369
 10. SUBJECT COMPLETION/WITHDRAWAL
  10.1 Completion
  10.2 Discontinuation of Treatment
  10.3 Withdrawal From the Study
 11. STATISTICAL METHODS
  11.1 Sample Size Determination
  11.2 Pharmacokinetics
  11.3 Efficacy Analysis
  11.4 Pharmacokinetic/Pharmacodynamic Analyses
  11.5 Safety Analyses
 12. ADVERSE EVENT REPORTING
 13. STUDY DRUG INFORMATION
 14. STUDY-SPECIFIC MATERIALS
 15. ETHICAL ASPECTS
 16. ADMINISTRATIVE REQUIREMENTS
 17. REFERENCES

| ATTACHMENTS |
| AMENDMENTS |

As shown above, template 391 includes both text and XML tags (although any alternative technique for organizing template 391 may also be implemented). For example, template 391 includes the XML tag <Company Name> in field 352. The XML tags <Company Name> identifies a portion of the template 391 for storing text associated with a company's name. That is, upon creation of document 310 from template 391 (e.g., by document creation sub-system 380) or at another convenient time (e.g., via manual revision sub-system 382), a user may enter the text "Johnson & Johnson" into document 310 in field 352 between the XML tags <Company Name>. As such, the string "Johnson & Johnson" is associated with the XML tag <Company Name>.

Continuing with template 391, it includes XML tags <READ ONLY> 354 surrounding field 353. The XML tag <READ ONLY> 354 marks a portion of document 310 as read-only. Thus, the text in field 353:

"INVESTIGATOR AGREEMENT I have read this agreement and agree that it contains all the necessary details for carrying out the study. I will conduct the study as outline herein and will complete the study within the time designated."

is marked as read-only in document 310. For fields that should not be edited or revised, the XML tag <READ ONLY> may be used to mark a portion of document 310 as read-only, preventing a user from revising that portion of document 310. By including such read-only tags, document 310 may thus include sections that are predefined as read-only.

Further, while the "read-only" text in field 353 may be stored in template 391 itself, the "read-only" text in field 353 may alternatively be stored in a separate database or data store (e.g., database 390) and the template 391 may include a pointer to the location of the "read-only" text to be "linked" to field 353. In this alternative case, upon document creation by document creation sub-system 380, document production system 185 may, using the pointer, determine the location of the "read-only" source text to be "linked" to field 353 and may display the "read-only" text in field 353 of document 310. In this alternative case, because the source text is not "copied" into document 310, if the source text (e.g., in database 390) is revised, the display in field 353 of document 310 may also be automatically revised (described in more detail below).

Template 391 further includes a highlighted field 355 for indicating to the user to make a manual entry of text (e.g., via manual revision sub-system 382). As shown, template 391 includes the text "[primary]" between XML tags <highlight>. When the text and the XML tags are copied to document 310 (e.g., via document creation sub-system 380), the XML tags <highlight> indicate to the XML editor to display the text "[primary]" with highlighting. The highlighted field may be displayed in document 310 as black text with a yellow background, or the like. The highlighting indicates to the user to manually edit document 310. In this manner, the user is prompted to decide whether to include or to delete the text "primary" from document 310. Template 391 includes other highlighted fields 357, 358, and 359, for example.

Template 391 further includes a reference to a protocol parameter reference <dts:function="ProtocolInformation/Parameters/textbox[@name='number of participants'] text( )"> in field 356. A protocol parameter is a parameter associated with a clinical protocol. Document production system 185 may generate a variable representing the protocol parameter, such that the protocol parameter may be automatically inserted or linked into document 310 as described in more detail below. The protocol parameter may be selected, for example, by the user via protocol parameter selection sub-system 384. For example, upon document creation (e.g., via document creation sub-system 380) or at other times, document production system 185 may interface with the user to receive user selection of a protocol parameter.

FIG. 4 shows an illustrative screen shot 400 of a user interface for protocol parameter selection sub-system 384. As shown in FIG. 4, the screen shot 400 includes a prompt for a selection of one of (a) a genetic testing parameter indicating a selection of one of Raritan testing, other testing, and no testing in screen portion 410, (b) a subject gender parameter indicating a selection of one of male only, female only, and male and female in screen portion 415, (c) a dose multiplicity parameter indicating a selection of one of single dose, single ascending dosage, and multiple dosages in screen portion 420, (d) a population parameter indicating a selection of healthy volunteers and other volunteers and both healthy and other volunteers in screen portion 425, (e) a case report form parameter indicating a selection of one of paper and electronic in screen portion 430, (f) a clinical trial location parameter indicating a selection of one of the United States and the European Union in screen portion 435, (g) a blinding model parameter indicating a selection of one of a single blind trial, a double blind trial, and an open-label trial in screen portion 440, (h) a number of participants parameter in screen portion 445, and (i) a number of treatment groups parameter in screen portion 450. Each screen portion in FIG. 4 has an area for user input, such as, for example, a text box, a selection area, and the like.

Thus, protocol parameter selection sub-system 384 may prompt for a number of study participants, for example, in screen portion 445. In response to the user entering a value into the user input area of screen portion 445, protocol parameter selection sub-system 384 may receive and store the user entered value (e.g., in database 390) and associate the stored value with a protocol parameter or variable named 'number of participants.' For example, if the user selects '15' in response to the prompt in screen portion 445, protocol parameter selection sub-system 384 may set the variable 'number of participants' to the value '15,' to the text string "fifteen," and the like. With this association, document production system 185 may read the reference to protocol parameter <dts:function="ProtocolInformation/Parameters/textbox [@name='number of participants'] text( )"> in field 356, determine the value associated with the parameter, and display (via copying or linking) the associated value as text in document 310. In this manner, the user may enter the number of participants only one time and document production system 185 may display the appropriate value in various places in document 310.

Returning again to template 391, it includes another protocol parameter reference <dts:function="ProtocolInformation/Parameters/textbox [@name='number of participants']text( )"> in field 361. Upon creation of document 310 (or at another convenient time), document production system 185 may read the protocol parameter reference in field 361 from template 391, determine the value associated with variable 'number of participants,' and display (via copying or linking) the associated value in document 310 in place of (or in addition to) protocol parameter field 361. In this manner, the value associated with the variable 'number of participants' may be displayed in many sections of document 310 (e.g., in field 356 and field 361), without requiring the user to re-enter the number of participants multiple times.

Template 391 includes another protocol parameter reference, namely, <dts:condition="not($raritanSamples)" dts:function"=$bloodQuantity"> in field 359. The reference in field 359 refers to two variables, i.e., 'raritanSamples' and 'bloodQuantity.' If the value associated with the variable 'raritanSamples' is TRUE, then the value associated with the variable 'bloodQuantity' is determined and displayed in document 310. If the value associated with the variable 'raritanSamples' is FALSE, then no value is displayed in document 310. The variable 'raritanSamples' may be set via protocol parameter selection sub-system 384 (e.g., via screen portion 410), may be predefined and stored in database 390, and the like. The variable 'bloodQuantity' may be set via protocol parameter selection sub-system 384, may be predefined and stored in database 390, and the like. Upon creation of document 310 (or at another convenient time), document production system 185 may read the protocol parameter reference from field 359 of template 391, determine the value associated with the variable 'bloodQunatity,' and display (via copying or linking) the value in document 310 in place of (or in addition to) the protocol parameter reference in field 359, if the variable 'raritanSamples' is TRUE. If the variable 'raritanSamples' is FALSE, document production system 185 may not display field 359.

Template 391 also includes protocol parameter reference <dts:function="ProtocolInformation/Parameters/textbox [@name='BlindingModel']text( )"> in field 362. The protocol parameter reference in field 362 is associated with a protocol parameter that may be selected by the user (e.g., via protocol parameter selection sub-system 384). FIG. 4 shows an illustrative screen shot 400 of a user interface for user selection of a clinical protocol parameter. As shown in FIG. 4, the screen shot 400 includes a prompt for a selection of a "BlindingModel" in screen portion 440. In response to the user selection to the prompt in screen portion 440, document production system 185 may cause a variable 'BlindingModel' to be set accordingly. That is, if the user selects 'Single Blind' in response to the prompt in screen portion 440, document production system 185 may set the variable 'BlindingModel' to the text string 'Single' and the like. Upon creation of document 310 (or at another convenient time), document production system 185 may read the protocol parameter reference from field 362 of template 391, determine the value (e.g., text string) associated with variable 'BlindingModel,' and display (via copying or linking) the value (e.g., text string) in document 310 in place of (or in addition to) field 362.

Figure 5:
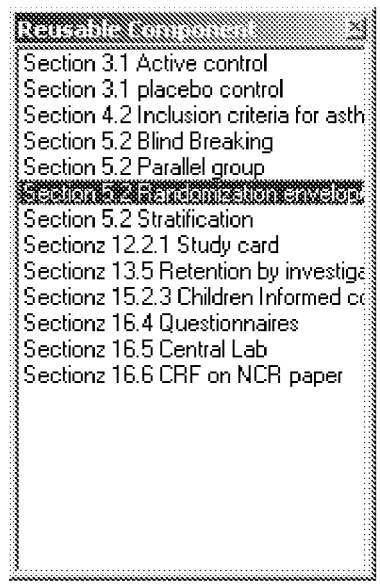
FIG. 5 is a screen shot of another illustrative user interface for production of a clinical protocol document, in accordance with an aspect of the invention.

Template 391 further includes an item "<highlight> Place for Drag and Drop Placebo control, if none DELETE. <highlight>" in field 363. The item in field 363 indicates to the user to insert a reusable component into document 310. That is, if the clinical protocol includes a placebo control group, the user may select to insert a particular reusable component into document 310. For example, document production system 185 may display the screen shot as shown in FIG. 5 and a user may select "Placebo Control." The user may then select a location in document 310 for insertion of a "Placebo Control" text. In response, document production system 185 displays (via copying or linking) the text associated with the "Placebo Control" of FIG. 5 in document 310. The text may be stored in the reusable component section 396 of database 390 or the like.

Template 391 further includes another protocol parameter reference <dts:function:"ProtocolInformation/Parameters/optionbutton[@name='SubjectGender']/item/text( )"> in field 364. Upon document creation 380 or at other times, document production system 185 may interface with the user to receive a user selection of a protocol parameter (e.g., via parameter selection sub-system 384). FIG. 4 shows an illustrative screen shot 400 of a user interface for user selection of a protocol parameter. As shown in FIG. 4, the screen shot 400 includes a prompt for a selection of a subject gender parameter indicating a selection of one of male only, female only, and male and female in screen portion 415. In response to the user selection to the prompt in screen portion 415, document production system 185 may cause the variable 'SubjectGender' to be set accordingly. That is, if the user selects Male Only in response to prompt 415, document production system 185 may set the variable 'SubjectGender' to the text string "Male Only." Upon creation of document 310 (or at another convenient time), document production system 185 may read the protocol parameter reference from field 364 of template 391, determine the value associated with variable 'SubjectGender,' and display (via copying or linking) the value in document 310 in place of (or in addition to) field 364.

Template 391 further includes another protocol parameter reference <dts:function:"ProtocolInformation/Parameters/optionbutton[@name='CaseReportForm']/item/text( )"> in field 365. As shown in FIG. 4, the screen shot 400 includes a prompt for a selection of a Case Report Form parameter indicating a selection of one of paper and EDC (electronic reporting) in screen portion 430. In response to the user selection to the prompt in screen portion 430, document production system 185 may cause the variable 'CaseReportForm' to be set accordingly. Upon creation of document 310 (or at another convenient time), document production system 185 may read the protocol parameter from field 365, determine the value associated with variable 'CaseReportForm,' and display (via copying or linking) the value in document 310 in place of (or in addition to) field 365.

Template 391 further includes another protocol parameter reference <dts:function: "ProtocolInformation/Parameters/optionbutton[@name='CaseReportForm']/item/text( )"> in field 366 that function similar to protocol parameter field 365. As can be seen, a single variable can be referenced multiple times in template 391. As such, the user is not required to input redundant information multiple time. Instead, the user may respond to a single prompt and document production system 185 may display appropriate text in multiple places in document 310.

Template 391 further includes a protocol reference <dts:function="$clinicalLaboratoryHematologyTables"> in field 367. The protocol reference in field 367 is associated with data or information. For example, the protocol reference in field 367 may be associated with a reference table stored in database 390 (e.g., general section 392). The reference table may be a table of hematology values to be used during the clinical trial. Upon creation of document 310 (or at another convenient time), document production system 185 may read protocol reference field 367, determine the data or information (e.g., table) associated with field 367, and display (via copying or linking) the data or information (e.g., table) associated with field 367 in document 310 in place of (or in addition to) field 367. Template 391 includes further protocol references <dts:

function="$clinicalLaboratoryBiochemistryTables"> in field 368 and <dts:function="$clinicalLaboratoryUrinalysisTables"> in field 369, which function similar to the protocol reference in field 367. Further, these tables may be inserted in document 310 upon receipt of a user selection of a corresponding medical test activity rather than being included in template 391.

Template 391 also includes an overall synopsis section 370 and a plurality of partial synopsis sections 371a and 371b. Partial synopsis sections 371a and 371b are synopses of each section of template 391. For example, partial synopsis section 371a is a synopsis of the "Objectives" section of template 391 and partial synopsis section 371b is a synopsis of the "Overview of the Study Design" section of template 391. Upon creation of document 310 (or at another convenient time), document production system 185 receives information into each of the plurality of partial synopsis sections 371a and 371b (e.g., via manual revision sub-system 382). When the information has been entered into each of the plurality of partial synopsis sections 371a and 371b (or at another convenient time such as when the document 310 is saved or the like), document production system 185 may copy the information associated with the plurality of partial synopsis sections 371a and 371b into the overall synopsis section 370 of document 310. As previously noted, the overall synopsis section 370 is marked with XML tags as read-only. Thus, the information displayed in the overall synopsis section of document 310 is not editable by the user of document 310. This allows consistency to be maintained between the overall synopsis section 370 and the partial synopsis sections 371a and 371b, even when the partial synopsis sections 371a and 371b have been revised over and over. The overall synopsis section 370 may further include information obtained via protocol parameter selection sub-system 384, charting sub-system 386, and the like (e.g., the protocol parameter representing the number of participants).

Document 310 may also include a chart section 312. Chart section 312 may include a chart that displays drug dosage information and medical assessment information in a time-activity chart format. For example, the chart may include an x-axis that represents time and a y-axis that represents drug dosages and medical assessment activity information (or vice-versa). FIG. 9 shows an illustrative time and events or activity chart 900. As shown in FIG. 9, the y-axis may include activities (e.g., drug dosages and medical assessment activity information), such as, a physical examination, weight and temperature assessment, serology, vital signs assessment, oral dose, etc. The x-axis may represent times, such as, a screening day, day −1 (the day prior to the first day of dosage, day 1 (the first day of dosage), day 2, etc.

Figure 6:
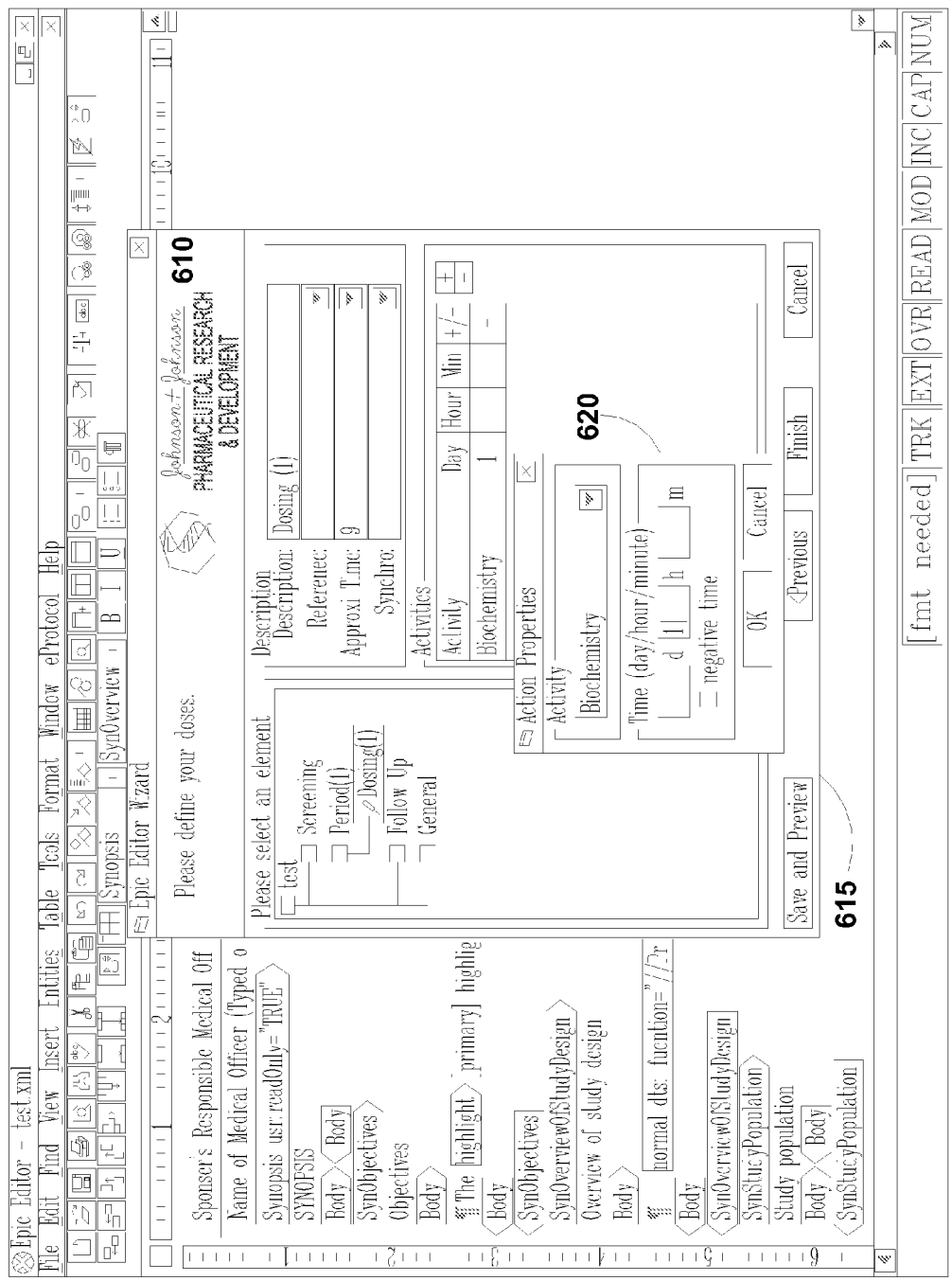
FIG. 6 is a screen shot of another illustrative user interface for production of a clinical protocol document, in accordance with an aspect of the invention.

The chart may be created by the user via charting sub-system 386. Charting sub-system 386 (or sub-system 386 in conjunction with user interface sub-system 389) may display the charting wizard shown in FIG. 6. As shown in FIG. 6, screen portion 610 of screen shot 600 includes a charting wizard that allows a user to input drug dosage and medical assessment activity information in a user-friendly chart format. Dosage information may include a drug name, a dosage amount, dosage administration type (e.g., needle, tablet, liquid, and the like), and dosage time. The charting sub-system 386 may set the dosage time to a particular time or may be link the dosage time to a previous dosage time. For example, the first dosage time may be set to 8:00 am EST. The second dosage time may be set to 9:00 am EST or may be set to one hour subsequent to the first dosage time. In this manner, the dosage times may be more easily revised (e.g., if the first dosage time is revised, the remaining dosage times may be automatically revised if their times depend on the first dosage time). Moreover, medical assessment activities may be scheduled such that are dependent on a first (or other) dosage time or may be dependent on another scheduled medical assessment activity.

Figure 7:
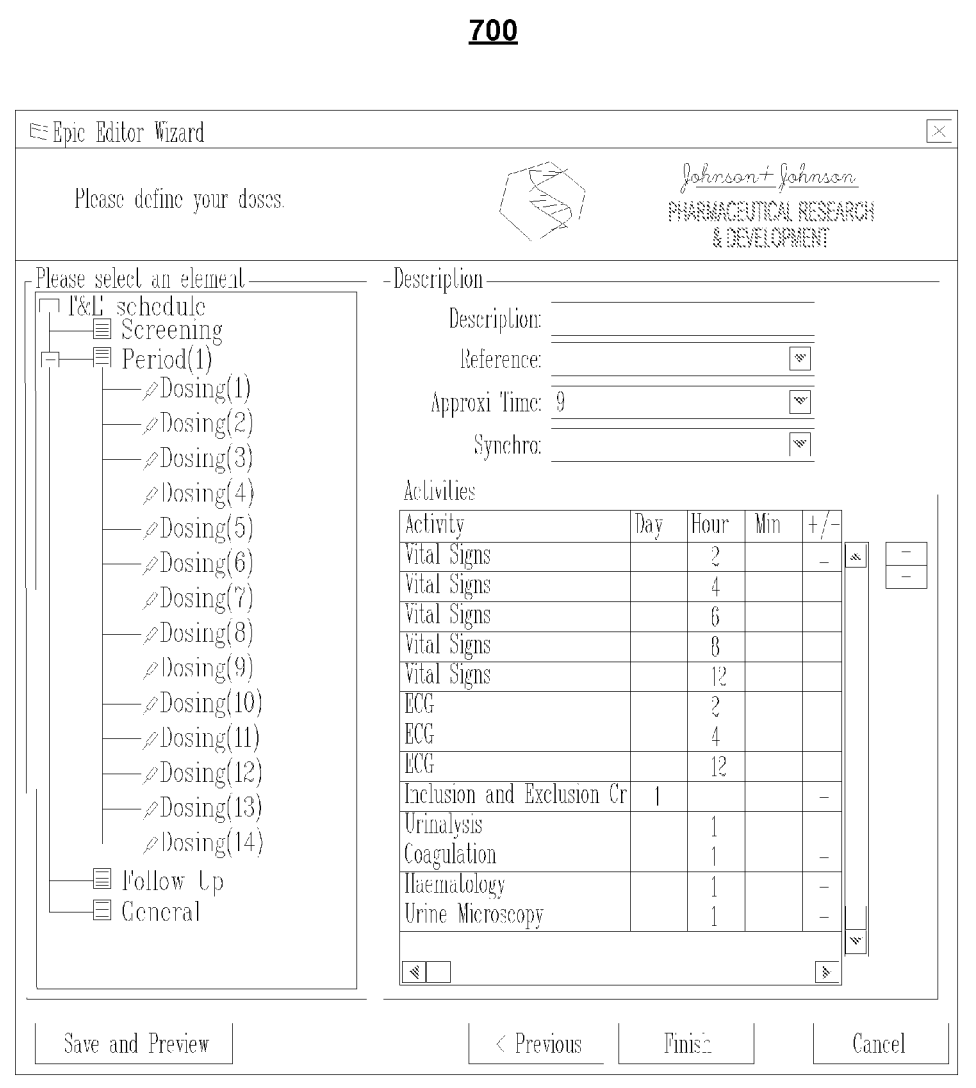

FIG. 7 shows another screen shot of an illustrative charting wizard 700. As shown in FIG. 7, dosage times are illustrated with icons of needles. Medical assessment activities could also be shown with appropriate icons, such as, stethoscopes, etc.

Charting sub-system 386 also allows a user (e.g., via the charting wizard) to input medical assessment activity information in a user-friendly chart format. Medical assessment activity information may include a medical assessment activity name, a medical assessment activity description, and medical assessment activity time. Charting sub-system 386 may set the medical assessment activity time to a particular time or link the medical assessment activity time to a dosage time or to another medical assessment activity time. For example, the first medical assessment activity time may be set to 8:00 am EST. The first medical assessment activity time may also be set to one hour prior to the first dosage time, one hour subsequent to the first dosage time, and the like. Charting sub-system 386 may set the medical assessment activity time by receiving user inputs via the user prompts in screen section 620. In screen section 620, the medical assessment activity time may be set by entering times into the day, hour, and minute fields. Checking the 'negative time' box causes charting sub-system 386 to link the medical assessment activity to a time prior to a drug dosage time (or activity). In this manner, the dosage and medical assessment activity times may be more easily revised (e.g., if the first dosage time is revised, the medical assessment activity times that are linked to the first dosage time may be automatically revised).

Charting sub-system 386 also allows a user (e.g., via the charting wizard) to select a medical assessment activity via the user prompts in screen section 620. For example, in screen portion 620, upon selection of 'Activity,' charting sub-system 386 may display a list of predefined medical assessment activities (e.g., biochemistry, vital signs, ECG, urinalysis, coagulation, hematology, and the like). The medical assessment activity may be selected by the user by clicking on one selection from the list predefined medical assessment activities.

Charting sub-system 386 also allows a user (e.g., via the charting wizard) to synchronize a medical assessment activity with a particular drug dosage time, via the user prompts in screen section 620. For example, in screen portion 610, upon selection of 'Syncro,' charting sub-system 386 may display a list of drug dosage times that have been entered by the user. Upon selection of one of the drug dosage times, charting sub-system 386 associates the medical assessment activities of the selected drug dosage time with the current drug dosage. To give an example, if the first drug dosage time had a vital signs medical assessment and a ECG recording linked one hour subsequent to the first drug dosage time, synchronizing a second drug dosage to the first drug dosage causes charting sub-system 386 to link a vital signs assessment and a ECG recording linked one hour subsequent to the second drug dosage time.

Charting sub-system 386 may switch between the charting wizard in screen portion 600 and a preview screen of the chart so that a user may review the drug dosage and medical assessment activity information in a user-friendly format. For example, upon user selection of "Save and Preview" button 610, charting sub-system 386 may display a preview of the chart including information that has already been entered via the charting wizard in screen portion 600. Such a chart preview is shown in FIG. 9.

Charting sub-system 386 may display drug dosages with color codes and icons. Because some medical assessment activities occur prior to a drug dosage while other medical assessment activities occur subsequent to a drug dosage, it may be confusing in chart form to determine which medical assessment activities are associated with which drug dosages. As such, charting sub-system 386 (and user interface sub-system 389) may display each medical assessment activity associated with a particular drug dosage using the same color. Further, each drug dosage or medical assessment activity may be displayed with an appropriate icon. For example, charting sub-system 386 may display drug dosages with a needle icon and the like. Charting sub-system 386 may display a vital signs medical assessment activity with a stethoscope and the like. Charting sub-system 386 may further display the chart with the time axis on the horizontal or vertical axis and may switch between the two displays upon receipt of a user request. Charting sub-system 386 may zoom in or out the chart display upon receipt of a user request.

Chart section 312 (or any section of document 310) may also include a text section that describes the drug dosage information and medical assessment activity information in a text format (i.e., the same information included in the chart, but in text format). Charting sub-system 386 may automatically or semi-automatically generate the text section that describes the drug dosage information and medical assessment activity information based on the information received via the charting wizard.

In automatic mode, charting sub-system 386 reads the drug dosage information and medical assessment activity information received via the charting wizard and automatically generates all of the text in the text section based on the received information. For example, charting sub-system 386 may determine the scheduled times of each of the drug dosages and medical assessment activities and order then chronologically. Then, charting sub-system 386 may, for each scheduled time, generate a sentence or a few sentences that describes the drug dosage or medical assessment activity associated with that time. Further, charting sub-system 386 may order the drug dosages and medical assessment activities in any order, and may organize the drug dosages and medical assessment activities in any fashion (such as by type of medical assessment activity).

Alternatively, in semi-automatic mode, charting sub-system 386 automatically generates a portion of the text in the text section and prompts the user to either select or enter additional information. For example, charting sub-system 386 may automatically generate and display the text "At the following times,_perform an ECG" then prompt the user to drag in a list of times from the chart section 312. Charting sub-system 386 may receive a selection of a section of the chart and convert the information in the selected section of the chart into text. Charting sub-system 386 may then insert the converted text into the text section. Further, charting sub-system 386 may generate text describing how to perform the drug dosage or medical assessment activity (e.g., by determining text associated with the drug dosage or medical assessment activity) and display and insert the generated text in the text section.

User interface sub-system 389 may display text in document 310 based on a variety of factors. For example, user interface sub-system 389 may display text in document 310 with different background colors based on where the text originated, based on the read-write status of the text, and the like. For example, if the displayed text originated from protocol parameter selection sub-system 384, the text may be displayed with a green background. If the displayed text originated from the template 391, the text may be displayed with a grey background. If the displayed text has a read-only status, the text may be displayed with a dark grey background. If the displayed text has a read-write status, the text may be displayed with a light grey background. If the displayed text has been revised (e.g., via manual revision sub-system 382), the text may be displayed with a white background. Upon selection of text via manual revision sub-system 382, the selected text may be displayed with a blue background and a prompt displayed requesting confirmation of manual revision of the selected text. Text originating from drug specific section 395 may be displayed with a purple background. Further, user interface sub-system 389 may display the section synopses between blue lines to indicate that the section synopses may be manually revised (e.g., via manual revision sub-system 382).

To track revisions, document production system 185 may provide for notes to be associated with document 310. Document production system 185 may display the notes on blocks of yellow background. Each document 310 may be associated with an author, a person with final signatory authority, and various reviewers. The author of the document 310 and person with final signatory authority may have appropriate security levels associated with revising and digitally signing document 310. For example, document production system 185 may allow reviewers to only add notes but not to accept or approve notes and not to modify document 310. Document production system 185 may allow the author to approve, delete, and modify a note. Further document production system 185 may require that all notes are either approved or deleted before allowing the person with final signatory authority to digitally sign the document 310 (thus indicating final approval of the protocol).

To track versions, document production system 185 may determine that some source text linked to document 310 has been revised (e.g., text in drug-specific section 395, reusable component section 397, and the like). Document production system 185 may indicate that new revised text is available for integration into document 310 and offer the options of accepting the new revised text or not accepting the new revised text. If document production system 185 receives a selection to accept the new revised text, document production system 185 may display the new revised text document 310 and maintain a link to the source text in case it is revised again in the future. If document production system 185 receives a selection to not accept the new revised text, document production system 185 may delete the link between document 310 and the source text, but continue to display the original source text in document 310. Document production system 185 may maintain version numbers on source text.

Figure 8:
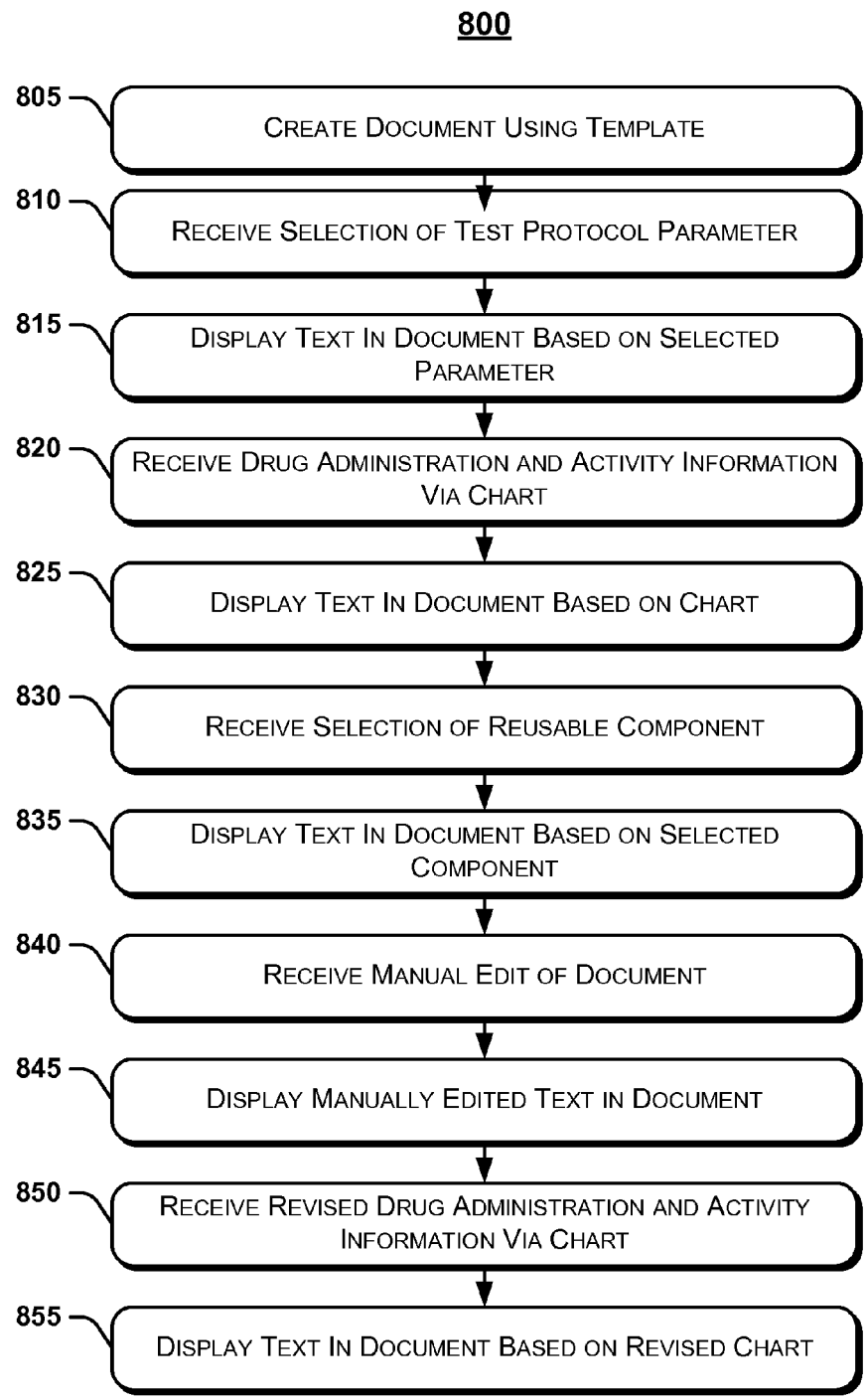
FIG. 8 is a flowchart of an illustrative method for production of a clinical protocol document, in accordance with an aspect of the invention.

Turning now to FIG. 8, it shows an illustrative method 800 for producing a clinical protocol document. While multiple steps are illustrated in FIG. 8, a portion of the steps may be executed by document production system 185 or any combination of steps may be executed by document production system 185. As shown in FIG. 8, at step 805, document production system 185 (e.g., document creation sub-system 380 and user interface sub-system 389) creates a document 310 using template 391 (and described in more detail above in connection with document creation sub-system 380 and user interface sub-system 389).

At step 810, document production system 185 (e.g., protocol parameter selection sub-system 384) receives a selection of a clinical protocol parameter (and described in more detail above in connection with protocol parameter selection sub-system 384 and user interface sub-system 389).

At step 815, document production system 185 (e.g., protocol parameter selection sub-system 384 and user interface sub-system 389) displays (via copying or linking) text in document 310 based on the parameter selected in step 810 (and described in more detail above in connection with protocol parameter selection sub-system 384 and user interface sub-system 389).

At step 820, document production system 185 (e.g., charting sub-system 386 and user interface sub-system 389) receives drug dosage information and medical assessment activity information via a chart interface (and described in more detail above in connection with protocol parameter selection sub-system 384 and user interface sub-system 389).

At step 825, document production system 185 (e.g., charting sub-system 386 and user interface sub-system 389) displays (via copying or linking) text in document 310 based on information received via the chart interface at step 820 (and described in more detail above in connection with protocol parameter selection sub-system 384 and user interface sub-system 389).

At step 830, document production system 185 (e.g., reusable component sub-system 388 and user interface sub-system 389) receives a selection of a reusable component (and described in more detail above in connection with reusable component sub-system 388 and user interface sub-system 389).

At step 835, document production system 185 (e.g., reusable component sub-system 388 and user interface sub-system 389) displays (via copying or linking) text in document 310 based on the selection received at step 820 (and described in more detail above in connection with reusable component sub-system 388 and user interface sub-system 389).

At step 840, document production system 185 (e.g., manual revision sub-system 382 and user interface sub-system 389) receives a manual revision to document 310 (and described in more detail above in connection with manual revision sub-system 382 and user interface sub-system 389).

At step 845, document production system 185 (e.g., manual revision sub-system 382 and user interface sub-system 389) displays (via copying or linking) text in document 310 based on the manual revision received at step 840 (and described in more detail above in connection with manual revision sub-system 382 and user interface sub-system 389).

At step 850, document production system 185 (e.g., charting sub-system 386 and user interface sub-system 389) receives revised drug dosage information and medical assessment activity information via a chart interface (and described in more detail above in connection with protocol parameter selection sub-system 384 and user interface sub-system 389).

At step 855, document production system 185 (e.g., charting sub-system 386 and user interface sub-system 389) displays (via copying or linking) revised text in document 310 based on revised information received via the chart interface at step 820 (and described in more detail above in connection with charting sub-system 386 and user interface sub-system 389). In this manner, the user may revise the chart via a user-friendly chart interface and have the text portion of document 310 correspond to the information received by the chart interface.

Aspects of the invention may be implemented via computer storage media and communication media. Computer storage media includes volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

Communication media typically embodies computer readable instructions, data structures, program modules, or other data in a modulated data signal, such as carrier wave or other transport mechanism. Communication media also includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above are also included within the scope of computer readable media.

As the foregoing illustrates, the invention is directed to the production of a clinical protocol document. It is understood that changes may be made to the illustrative embodiments described above without departing from the broad inventive concepts disclosed herein. Accordingly, it is understood that the invention is not limited to the particular embodiments disclosed, but is intended to cover all modifications that are within the spirit and scope of the invention as defined by the appended claims.

What is claimed:

1. A method for processing clinical protocol document information comprising chart information and text information, the chart information for displaying drug dosage information and medical assessment activity information in a time-activity chart format, the text information for describing the drug dosage information and medical assessment activity information in a text format, the method comprising:

storing source text and one or more templates comprising predetermined text for generating said drug dosage information and medical assessment activity information in at least one data store;

generating a charting user interface on a display device, wherein the charting user interface is configured to allow a user to enter said drug dosage information and medical assessment activity information;

providing, via said charting user interface, both an automatic mode and a semi-automatic mode, and receiving said medical drug dosage information and medical assessment activity information via said charting user interface, wherein:

when said charting user interface is configured to execute in the automatic mode, based on the received medical drug dosage information and medical assessment activity information, automatically generating text describing the received medical drug dosage information and medical assessment activity information by using said source text and said one or more templates in said at least one data store, wherein changes to the received medical drug dosage information and medical assessment activity information cause a corresponding change to the text without manually entering the the text; and when said charting user interface is configured to execute in the semi-automatic mode, based on the received medical drug dosage information and medical assessment activity information, automatically generating a first portion of the text describing the received medical drug dosage information and medical assessment activity information by using said source text and said one or more templates in said at least one data store, prompting the user to select or enter additional information, and using the additional information to generate a second portion of the text describing the received medical drug dosage information and medical assessment activity information, wherein changes to the received medical drug dosage information and medical assessment activity information cause a corresponding change to the first and second portions of the text without manually entering the first and second portions of the text;

displaying said clinical protocol document information on the display device by displaying the medical drug dosage information and medical assessment activity information in the time-activity chart format; and displaying the text in the text format, wherein the text is displayed in accordance with at least one of said templates and said predetermined text is displayed in a different format from other text.

2. The method as recited in claim 1, wherein the received medical drug dosage information comprises a first drug dosage amount and a first time for administering the first drug dosage amount.

3. The method as recited in claim 2, wherein the received medical drug dosage information comprises a second drug dosage amount and, for administering the second drug dosage amount, an incremental time from the first time for administering the first drug dosage amount.

4. The method as recited in claim 2, wherein the received medical assessment activity information comprises an incremental time from the first time for administering the first drug dosage amount.

5. The method as recited in claim 1, wherein the received medical assessment activity information comprises one of a vital sign measurement, an electroencephalogram, and a urinalysis.

6. The method as recited in claim 1, wherein said automatically generating comprises identifying text in a database corresponding to the received medical assessment activity information.

7. The method as recited in claim 1, further comprising:
receiving a clinical protocol parameter;
determining text based on the received clinical protocol parameter; and
displaying the determined text.

8. The method as recited in claim 1, wherein said automatically generating comprises identifying text in a database corresponding to the received medical drug dosage information and medical assessment activity information.

9. The method as recited in claim 8, wherein the medical drug dosage information and medical assessment activity information comprises one of (a) a genetic testing parameter indicating a selection of one of Raritan testing and other testing, (b) a gender parameter indicating a selection of one of male only, female only, and male and female, (c) a dose multiplicity parameter indicating a selection of one of single dose, single ascending dosage, and multiple dosages, (d) a population parameter indicating a selection of healthy volunteers and other volunteers, (e) a clinical trial location parameter indicating a selection of one of the United States and the European Union, (f) a blinding model parameter indicating a selection of one of a single blind trial, a double blind trial, and an open-label trial, and (g) a number of participants.

10. The method as recited in claim 1, further comprising:
receiving a selection of a reusable text component;
determining text based on the selected reusable text component; and
displaying the determined text.

11. The method as recited in claim 1, further comprising:
generating a plurality of sections, wherein each of the plurality of sections comprises a synopsis of the section;
combining the synopses of each of the plurality of sections to generate an overall clinical protocol synopsis; and
displaying the overall clinical protocol synopsis.

12. The method as recited in claim 11, wherein said generating comprises organizing the clinical protocol document information into a plurality of sections via Extensible Markup Language (XML) tags.

13. The method as recited in claim 1, wherein the template comprises XML tags organizing the document information into a plurality of sections and organizing each section into a plurality of fields, and further comprising:
displaying the predetermined text using a first color; and
displaying the generated text using a second color.

14. The method as recited in claim 1, further comprising:
determining a plurality of portions of the clinical protocol document information that are not manually editable;
displaying the portions of the clinical protocol document information that are not manually editable using a first color;
determining a plurality of portions of the clinical protocol document information that are manually editable; and
displaying the portions of the clinical protocol document information that are manually editable using a second color.

15. The method as recited in claim 14, further comprising:
receiving edits to one of the plurality of portions of the clinical protocol document information that are manually editable; and
displaying the edited portion of the clinical protocol document information with no color to indicate that the portion has been edited.

16. A tangible computer-readable storage medium having computer-readable instructions stored thereon for processing clinical protocol document information comprising chart information and text information, the chart information for displaying drug dosage information and medical assessment activity information in a time-activity chart format, the text information for describing the drug dosage information and medical assessment activity information in a text format, the instructions when executed on a processor causing the processor to perform the following:
storing source text and one or more templates comprising predetermined text for generating said drug dosage information and medical assessment activity information in at least one data store;
generating a charting user interface on a display device, wherein the charting user interface is configured to allow a user to enter said drug dosage information and medical assessment activity information;
providing, via, via said charting user interface, both an automatic mode and a semi-automatic mode, and receiving said medical drug dosage information and medical assessment activity information via said charting user interface, wherein:
when said charting user interface is configured to execute in the automatic mode, based on the received medical drug dosage information and medical assessment activity information, automatically generating text describing the received medical drug dosage information and medical assessment activity information by using said source text and said one or more templates in said at least one data store, wherein changes to the received medical drug dosage information and medical assessment activity information cause a corresponding change to the text without manually entering the the text;

when said charting user interface is configured to execute in the semi-automatic mode, based on the received medical drug dosage information and medical assessment activity information, automatically generating a first portion of the text describing the received medical drug dosage information and medical assessment activity information by using said source text and said one or more templates in said at least one data store, prompting the user to select or enter additional information, and using the additional information to generate a second portion of the text describing the received medical drug dosage information and medical assessment activity information, wherein changes to the received medical drug dosage information and medical assessment activity information cause a corresponding change to the first and second portions of the text without manually entering the first and second portions of the text;

displaying said clinical protocol document information on the display device by displaying the medical drug dosage information and medical assessment activity information in the time-activity chart format; and displaying the text in the text format, wherein the text is displayed in accordance with at least one of said templates and said predetermined text is displayed in a different format from other text.

17. The tangible computer-readable storage medium as recited in claim 16, wherein the received medical drug dosage information comprises a first drug dosage amount and a first time for administering the first drug dosage amount.

18. The tangible computer-readable storage medium as recited in claim 17, wherein the received medical drug dosage information comprises a second drug dosage amount and, for administering the second drug dosage amount, an incremental time from the first time for administering the first drug dosage amount.

19. The tangible computer-readable storage medium as recited in claim 17, wherein the received medical assessment activity information comprises an incremental time from the first time for administering the first drug dosage amount.

20. The tangible computer-readable storage medium as recited in claim 16, wherein the received medical assessment activity information comprises one of a vital sign measurement, an electroencephalogram, and a urinalysis.

21. The tangible computer-readable storage medium as recited in claim 16, wherein said automatically generating comprises identifying text in a database corresponding to the received medical assessment activity information.

22. The tangible computer-readable storage medium as recited in claim 16, wherein the instructions further cause the processor to perform the following:
receiving a clinical protocol parameter;
determining text based on the received clinical protocol parameter; and
displaying the determined text.

23. The tangible computer-readable storage medium as recited in claim 16, wherein c automatically generating comprises identifying text in a database corresponding to the received medical drug dosage information and medical assessment activity information.

24. The tangible computer-readable storage medium as recited in claim 23, wherein the medical drug dosage information and medical assessment activity information comprises one of (a) a genetic testing parameter indicating a selection of one of Raritan testing and other testing, (b) a gender parameter indicating a selection of one of male only, female only, and male and female, (c) a dose multiplicity parameter indicating a selection of one of single dose, single ascending dosage, and multiple dosages, (d) a population parameter indicating a selection of healthy volunteers and other volunteers, (e) a clinical trial location parameter indicating a selection of one of the United States and the European Union, (f) a blinding model parameter indicating a selection of one of a single blind trial, a double blind trial, and an open-label trial, and (g) a number of participants.

25. The tangible computer-readable storage medium as recited in claim 16, wherein the instructions further cause the processor to perform the following:
receiving a selection of a reusable text component;
determining text based on the selected reusable text component; and
displaying the determined text.

26. The tangible computer-readable storage medium as recited in claim 16, wherein the instructions further cause the processor to perform the following:
generating a plurality of sections, wherein each of the plurality of sections comprises a synopsis of the section;
combining the synopses of each of the plurality of sections to generate an overall clinical protocol synopsis; and
displaying the overall clinical protocol synopsis.

27. The tangible computer-readable storage medium as recited in claim 26, wherein said generating comprises organizing the clinical protocol document information into a plurality of sections via Extensible Markup Language (XML) tags.

28. The tangible computer-readable storage medium as recited in claim 16, wherein the template comprises XML tags organizing the document information into a plurality of sections and organizing each section into a plurality of fields, and wherein the instructions further cause the processor to perform the following:
displaying the predetermined text using a first color; and
displaying the generated text using a second color.

29. The tangible computer-readable storage medium as recited in claim 16, wherein the instructions further cause the processor to perform the following:
determining a plurality of portions of the clinical protocol document information that are not manually editable;
displaying the portions of the clinical protocol document information that are not manually editable using a first color;
determining a plurality of portions of the clinical protocol document information that are manually editable; and
displaying the portions of the clinical protocol document information that are manually editable using a second color.

30. The tangible computer-readable storage medium as recited in claim 29, wherein the instructions further cause the processor to perform the following:
receiving edits to one of the plurality of portions of the clinical protocol document information that are manually editable; and
displaying the edited portion of the clinical protocol document information with no color to indicate that the portion has been edited.

31. A system for producing a clinical protocol document, the system comprising:
a document creation sub-system configured to generate clinical protocol document information comprising chart information and information text, the chart information for displaying drug dosage information and medical assessment activity information in a time-activity chart format, the text information for describing the drug dosage information and medical assessment activity information in a text format;

at least one data store having stored thereon source text and one or more templates comprising predetermined text for generating said drug dosage information and medical assessment activity information;

a charting sub-system configured to:
  allow a user to enter and revise said drug dosage information and medical assessment activity information in a chart form;
  provide, via said charting sub-system, both an automatic mode and a semi-automatic mode, and receive said medical drug dosage information and medical assessment activity information via said charting sub-system, wherein:
    when said charting sub-system is configured to execute in the automatic mode, based on the received medical drug dosage information and medical assessment activity information, automatically generate text describing the received medical drug dosage information and medical assessment activity information by using said source text and said one or more templates in said at least one data store, wherein changes to the received medical drug dosage information and medical assessment activity information cause a corresponding change to the text without manually entering the text; and
    when said charting sub-system is configured to execute in the semi-automatic mode, based on the received medical drug dosage information and medical assessment activity information, automatically generate a first portion of the text describing the received medical drug dosage information and medical assessment activity information by using said source text and said one or more templates in said at least one data store, prompting the user to select or enter additional information, and using the additional information to generate a second portion of the text describing the received medical drug dosage information and medical assessment activity information, wherein changes to the received medical drug dosage information and medical assessment activity information cause a corresponding change to the first and second portions of the text without manually entering the first and second portions of the text; and
  a user interface sub-system configured to:
  display the medical drug dosage information and medical assessment activity information in the time-activity chart format; and
  display the text in the text format, wherein the text is displayed in accordance with at least one of said templates and said predetermined text is displayed in a different format from other text.

32. The system as recited in claim 31, wherein the received medical drug dosage information comprises a first drug dosage amount and a first time for administering the first drug dosage amount.

33. The system as recited in claim 32, wherein the received medical drug dosage information comprises a second drug dosage amount and, for administering the second drug dosage amount, an incremental time from the first time for administering the first drug dosage amount.

34. The system as recited in claim 32, wherein the received medical assessment activity information comprises an incremental time from the first time for administering the first drug dosage amount.

35. The system as recited in claim 31, wherein the received medical assessment activity information comprises one of a vital sign measurement, an electroencephalogram, and a urinalysis.

36. The system as recited in claim 31, wherein the charting sub-system identifies text in a database corresponding to the received medical assessment activity information.

37. The system as recited in claim 31, further comprising:
a protocol parameter selection sub-system configured to:
  receive a clinical protocol parameter;
  determine text based on the received clinical protocol parameter; and
wherein the user interface sub-system displays the determined text.

38. The system as recited in claim 31, wherein the charting sub-system is further configured to identify text in a database corresponding to the received medical drug dosage information and medical assessment activity information.

39. The system as recited in claim 31, wherein the medical drug dosage information and medical assessment activity information comprises one of (a) a genetic testing parameter indicating a selection of one of Raritan testing and other testing, (b) a gender parameter indicating a selection of one of male only, female only, and male and female, (c) a dose multiplicity parameter indicating a selection of one of single dose, single ascending dosage, and multiple dosages, (d) a population parameter indicating a selection of healthy volunteers and other volunteers, (e) a clinical trial location parameter indicating a selection of one of the United States and the European Union, (f) a blinding model parameter indicating a selection of one of a single blind trial, a double blind trial, and an open-label trial, and (g) a number of participants.

40. The system as recited in claim 31, further comprising:
a reusable component sub-system configured to:
  receive a selection of a reusable text component; and
  determine a third portion of text based on the selected reusable text component;
wherein the user interface sub-system is further configured to display the third portion of text.

41. The system as recited in claim 31, wherein the document creation sub-system is further configured to:
generate a plurality of sections, wherein each of the plurality of sections comprises a synopsis of the section; and
combine the synopses of each of the plurality of sections to generate an overall clinical protocol synopsis; and
wherein the user interface sub-system is further configured to display the overall clinical protocol synopsis.

42. The system as recited in claim 41, wherein the document creation sub-system is further configured to organize the clinical protocol document information into a plurality of sections via Extensible Markup Language (XML) tags.

43. The system as recited in claim 31, wherein the template comprises XML tags organizing the document information into a plurality of sections and organizing each section into a plurality of fields, and the user interface sub-system is further configured to:
display the predetermined text using a first color; and
display the generated text using a second color.

44. The system as recited in claim 31, further comprising:
a manual revision sub-system configured to:
- determine a plurality of portions of the clinical protocol document information that are not manually editable; and
- determine a plurality of portions of the clinical protocol document information that are manually editable;

and wherein the user interface sub-system is further configured to:
- display the portions of the clinical protocol document information that are not manually editable using a first color; and
- display the portions of the clinical protocol document information that are manually editable using a second color.

45. The system as recited in claim 44, wherein the manual revision sub-system is further configured to:
- receive edits to one of the plurality of portions of the clinical protocol document information that are manually editable; and
- wherein the user interface sub-system is further configured to display the edited portion of the clinical protocol document information with no color to indicate that the portion has been edited.

46. The method as recited in claim 1, wherein said charting user interface is further configured to synchronize a selected medical assessment activity with a selected drug dosage time, further comprising, upon selection of the selected drug dosage time, automatically associating the selected medical assessment activity with a current drug dosage.

* * * * *

UNITED STATES PATENT AND TRADEMARK OFFICE
CERTIFICATE OF CORRECTION

| | |
|---|---|
| PATENT NO. | : 8,670,992 B2 |
| APPLICATION NO. | : 11/166989 |
| DATED | : March 11, 2014 |
| INVENTOR(S) | : Morlet et al. |

It is certified that error appears in the above-identified patent and that said Letters Patent is hereby corrected as shown below:

In the Claims

COL. 18 (Claim 1), line 62, delete first occurrence of "the"

COL. 20 (Claim 16), line 56, delete "via,"

Signed and Sealed this
Tenth Day of May, 2016

Michelle K. Lee
*Director of the United States Patent and Trademark Office*